United States Patent
Callahan (10) Patent No.: US 6,702,751 B2
(45) Date of Patent: Mar. 9, 2004

(54) METHOD AND SYSTEM FOR OPTIMALLY TIMING SCANS OF A SELECTED PART OF A PATIENT

(75) Inventor: Terrance Callahan, Aurora (CA)

(73) Assignee: Dicomit Dicom Information Technologies, Corp., Markham (CA)

( * ) Notice: Subject to any disclaimer, the term of this patent is extended or adjusted under 35 U.S.C. 154(b) by 325 days.

(21) Appl. No.: 09/891,536

(22) Filed: Jun. 27, 2001

(65) Prior Publication Data

US 2003/0167009 A1 Sep. 4, 2003

(51) Int. Cl.$^7$ ................................................ A61B 5/02
(52) U.S. Cl. .................. 600/481; 600/443; 600/411; 600/415; 600/407; 382/131; 345/419
(58) Field of Search ................................ 600/481, 443, 600/444, 445, 446, 447, 410, 411, 415, 425, 427, 407, 409, 453, 454, 455, 456; 382/128, 131, 154; 345/419, 420, 421, 427, 426; 378/4, 21, 25; 128/922

(56) References Cited

U.S. PATENT DOCUMENTS

| | | | | |
|---|---|---|---|---|
| 4,245,646 A | * | 1/1981 | Ionnou et al. ............... | 600/407 |
| 5,274,549 A | * | 12/1993 | Almasi ....................... | 382/128 |
| 5,485,839 A | * | 1/1996 | Aida et al. .................. | 600/427 |
| 5,505,204 A | * | 4/1996 | Picot et al. ................. | 600/456 |
| 5,590,653 A | * | 1/1997 | Aida et al. .................. | 600/411 |
| 5,897,495 A | * | 4/1999 | Aida et al. .................. | 600/411 |
| 6,256,037 B1 | * | 7/2001 | Callahan ..................... | 345/419 |
| 6,341,174 B1 | * | 1/2002 | Callahan et al. ............ | 382/154 |
| 6,342,889 B1 | * | 1/2002 | Callahan ..................... | 345/427 |

* cited by examiner

*Primary Examiner*—Henry Bennett
*Assistant Examiner*—Fadi H. Dahbour
(74) *Attorney, Agent, or Firm*—Dinesh Agarwal, P.C.

(57) ABSTRACT

A scanning system for obtaining an optimal image of a selected part of a patient, wherein the selected part varies cyclically over time. The scanning system comprises (1) scanner for scanning a cross-section of a selected part of the patient to generate a time-wise series of images of the cross-section; (2) image processing submodule for analyzing the time-wise series of images to determine a state of the selected part as shown in each image in the time-wise series of images; (3) image selection submodule for selecting the optimal image from the time-wise series of images based on the state of the selected part in the optimal image; and, (4) memory for storing the optimal image.

20 Claims, 6 Drawing Sheets

METHOD AND SYSTEM FOR OPTIMALLY TIMING SCANS OF A SELECTED PART OF A PATIENT

FIELD OF THE INVENTION

The present invention relates generally to scanning a patient to obtain images of a selected part of a patient, and, more particularly, to a method and system for generating optimal images of a selected part of a patient.

BACKGROUND OF THE INVENTION

In the medical field, scanning technologies such as ultrasound, x-ray and magnetic resonance imaging are used to obtain images of internal parts of a patient. These images are useful to physicians and other health professionals to assist them in assessing the patient's condition and deciding on appropriate medical treatment. Such scanning technologies can be used, for example, to view a foetus, blood flow patterns in arteries, or to scan organs for irregularities such as cysts.

A human body is a dynamic system, in that parts of the human body change over time. In many cases these changes are cyclical. For example, in the case of a blood vessel the dimensions of the blood vessel will change markedly depending on the amount of blood that is flowing through the blood vessel at a particular time. The amount of blood that flows through a blood vessel at a particular time depends, in part, on when the particular time occurs relative to the heartbeat or cardiac cycle of the patient. Specifically, when the patient's heart forces out blood, there is a surge of blood through the blood vessels and the blood vessels are dilated; however, when the heart is relaxing after each heartbeat, the amount of blood flowing through the blood vessels is substantially reduced, and the blood vessels are no longer as dilated. Organs, such as the heart itself, will also differ in appearance markedly depending on when they are viewed relative to the pumping action of the heart.

When tracking dynamic parts of a patient, it is easy to be deceived regarding the condition of these parts due to their dynamic character. Returning to the blood vessel example, when scanning a blood vessel it is easy to be deceived regarding the condition of the blood vessel by the fact that blood is pulsing through the blood vessel. Say, for example, that a blood vessel is being scanned for points of constriction where blood flow is blocked. As the flow of blood through a blood vessel fluctuates due to the pumping action of the heart, there will be periods when there is very little blood flowing through the blood vessel. As the blood vessel pulsates with the fluctuation of blood flowing therethrough, the dimensions of the blood vessel will also vary. If a cross-sectional frame of data is obtained by scanning a cross-section of a blood vessel when there is an ebb in the flow of blood through that point of the blood vessel, then the blood vessel will have a much smaller diameter then it would have had when the flow of blood through the blood vessel is at its maximum. To one viewing an image constructed from a cross-sectional frame of data thus obtained, it may appear that a blood vessel is constricted, when, in fact, the blood vessel is not constricted, but is merely being viewed at a time in the blood flow cycle when there is an ebb in blood flow. Alternatively, it may be difficult to determine if the blood vessel is truly constricted, as one examining an image constructed from a cross-sectional frame of data will be aware that what appears to be a constriction may, in actuality, be due to an ebb in the flow of blood through the blood vessel.

Accordingly, there is a need for a system and method of coordinating the scanning of a part of a patient with body cycles in order for a scan to be taken at an optimal time relative to those body cycles.

BRIEF SUMMARY OF THE INVENTION

An object of an embodiment of the present invention is to provide a system for obtaining an optimally-timed image of a selected part of a patient.

According to an embodiment of the present invention there is provided a scanning system for obtaining an optimal image of a selected part of a patient, wherein the selected part varies cyclically over time. The scanning system comprises (1) scanning means for scanning a cross-section of a selected part of the patient to generate a time-wise series of images of the cross-section; (2) image processing means for analyzing the time-wise series of images to determine a state of the selected part as shown in each image in the time-wise series of images; (3) image selection means for selecting the optimal image from the time-wise series of images based on the state of the selected part in the optimal image; and, (4) memory for storing the optimal image.

An object of one aspect of the present invention is to provide a method of obtaining an optimal image of a selected part of a patient at an optimal time.

According to one aspect of the present invention there is provided a method of obtaining an optimal image of a selected part of a patient being scanned, wherein the selected part varies cyclically over time. The method comprises the steps of (1) scanning the selected part to obtain a time-wise series of images of the selected part; (2) analyzing each image in the time-wise series of images to determine a state of the selected part as shown in that image of the time-wise series of images; and, (3) selecting a selected image from the time-wise series of images based on the state of the selected part in the selected image.

According to another aspect of the present invention there is provided a method of obtaining a plurality of images of a selected part of a patient being scanned by scanning the patient at a plurality of cross-sections, wherein the selected part varies cyclically over time. The method comprises the steps of, at each cross-section in the plurality of cross-sections, (a) scanning the patient to obtain an associated time-wise series of images of the selected part, (b) for each image in the associated time-wise series of images, analyzing the image to identify an state of the selected part at the cross-section, and (c) selecting an associated selected image from the associated time-wise series of images based on the state of the selected part at the cross-section in the associated selected image.

BRIEF DESCRIPTION OF THE DRAWINGS

Reference will now be made, by way of example, to the accompanying drawings, which show preferred aspects of the present invention, and in which like reference numerals refer to like structural components throughout.

DETAILED DESCRIPTION OF THE PREFERRED EMBODIMENTS OF THE INVENTION

Figure 1:
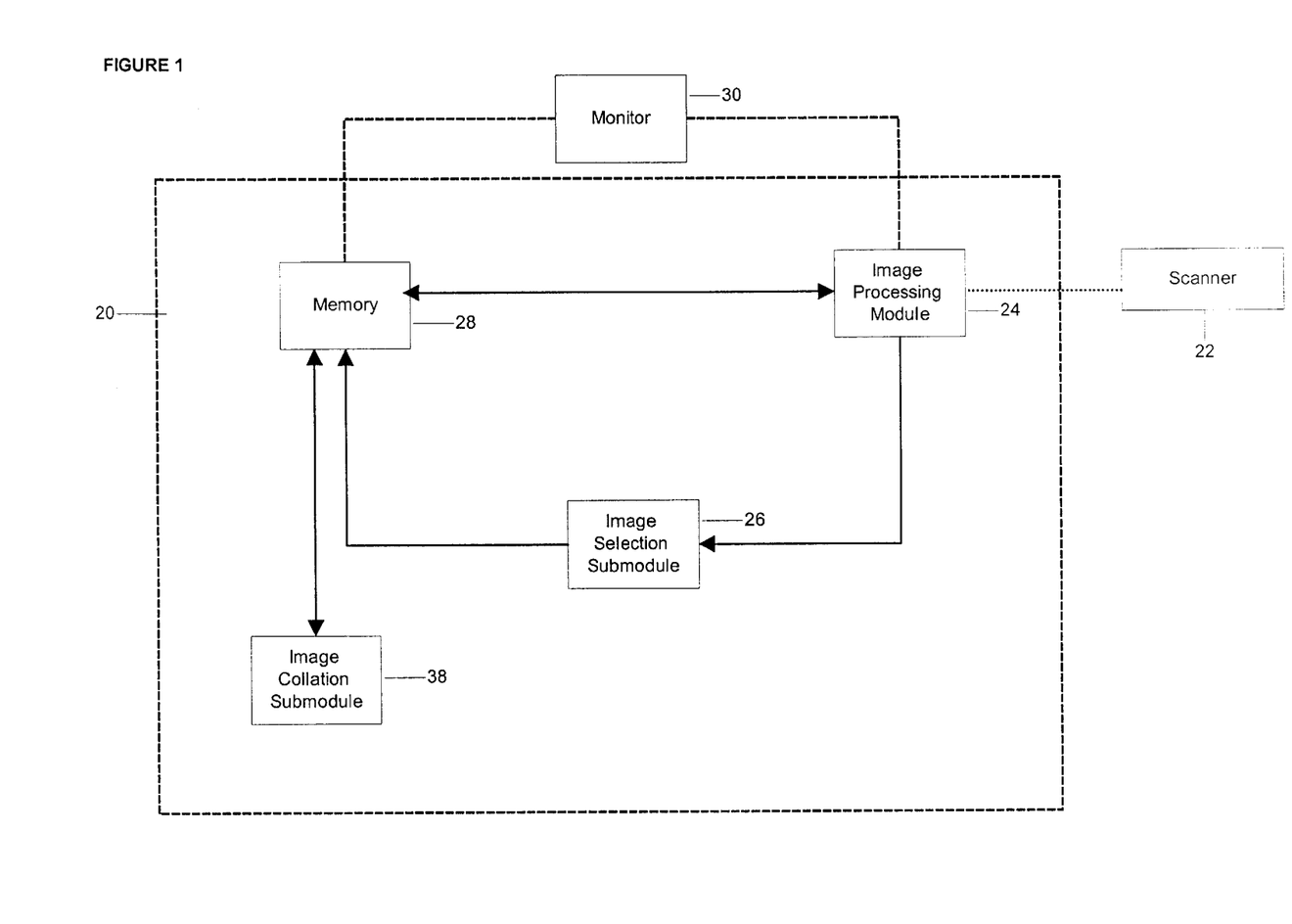
FIG. 1 is a block diagram showing a system for obtaining an optimal image of a part of a patient according to an embodiment of the present invention.

Referring to FIG. 1 there is illustrated a block diagram of a computer system 20 for providing an optimal image of a selected part of a patient in accordance with a preferred embodiment of the invention. The computer system 20 includes a scanner 22 that utilizes ultrasound, x-ray, magnetic resonance or other medical scanning technology.

As shown in FIG. 1, the scanner 22 is linked to an image processing submodule 24 of the system 20. The image processing submodule 24 is, in turn, linked to an image selection submodule 26, which is linked to a memory 28. The memory 28 is linked to an image collation submodule 38.

In operation, a selected part of the patient is scanned by the scanner 22 and the image data is then sent to the image processing submodule 24 where the scan data is processed. The processed data is then sent to the image selection submodule 26 of the computer system 20. The image selection submodule 26 determines whether the scanned image of the selected part of the patient was obtained at an optimal time interval within a natural cycle in the patient's body that affects the selected part of the patient.

Specifically, where, for example, a patient's blood vessel is being scanned by the scanner 22, the blood vessel is scanned by scanning a lengthwise series of cross-sections of the blood vessel. At each cross-section of the blood vessel in the lengthwise series of cross-sections, a time-wise series of scans are made. From each time-wise series of scans, an associated time-wise series of images are generated. From this associated time-wise series of images, an optimal image is selected and captured based on the state of the blood vessel shown in the image. Which image is selected as the optimal image will depend on the circumstances. For example, in order to ensure that the blood vessel is not constricting blood flow, the optimal image might be from a scan when the blood vessel is fully dilated. Then the image selection submodule 26 will determine whether a particular image generated by the image processing submodule 24 from the scan data received from the scanner 22 was taken when the blood vessel was fully dilated. The scan when the blood vessel was fully dilated could be determined by comparing the images of the blood vessel at different times, and selecting the image in which the dilation of the blood vessel is greatest. The image selection submodule 26 may, for example, make this determination by comparing each image with other images to determine which image shows the blood vessel at its most dilated.

In some circumstances, it will be unimportant when the optimal time is selected relative to the cyclical changes the dynamic part undergoes. In the blood vessel example, it may, for example, be unimportant for some purposes whether the scans are performed when the blood vessel is dilated or not; however, it may nonetheless be important that the lengthwise series of scans of the blood vessel all be taken at roughly the same point in the pulsating cycle of the blood vessel as otherwise it may be difficult to distinguish actual lengthwise variation in the cross-sectional images of the blood vessel from merely apparent lengthwise variation in the cross-sectional images of the blood vessel due to different scans in the lengthwise series of scans of the blood vessel being taken at different points in the cardiac cycle. Alternatively, it may be desirable for some diagnostic purposes to take different cross-sectional scans at different points in the cardiac cycle.

For each cross-section of the blood vessel in the lengthwise series of cross-sections, a sub-series of optimal images may be selected from the time-wise series of optimal images taken by the scanner 22 of the computer system 20. The sub-series of optimal images are taken over an entire cardiac cycle of the patient. The sub-series of optimal images are then ordered in a definite order depending on the point in the cardiac cycle at which they were taken. For example, the image of the blood vessel minimally dilated can be placed first in the sub-series followed by images of the blood vessel as it gradually dilates, each of which images is more dilated than the image preceding it in the sub-series, until the maximally dilated image is reached. The maximally dilated image in the sub-series is followed by images of the blood vessel as it gradually contracts, each of which images is more contracted than the image preceding it in the sub-series, until the minimally dilated image is once again reached. After all of the cross-sections of the blood vessel have been scanned and a sub-series of optimal images have been selected for each cross-section and have been saved in memory 28, the sub-series of optimal images of adjoining cross-sections are collated by the image collation submodule 38 by joining optimal images that are in the same place in the ordered sub-series of images. For example, an optimal image of a blood vessel at an $n_{th}$ cross-section that shows the blood vessel at its least dilated is joined with an optimal image of a blood vessel at an $(n+1)_{th}$ cross-section that also shows the blood vessel at its least dilated. By so joining all of the sub-series of optimal images, a dynamic image of the blood vessel showing the relative dilation of the entire blood vessel over the entire cardiac cycle can be constructed. Alternatively, if desired, the sub-series of optimal images of adjoining cross-sections may be collated by joining optimal images that are in different places in the ordered sub-series of images. This too will form a dynamic image of the blood vessel; however, at any instant different lengthwise portions of the dynamic image will be at different points in the cardiac cycle.

In conducting a scan, an operator will move the scanner 22 along a patient to scan the selected part of the patient at different points or cross-sections, which, taken together define a path along the patient. At each point along the path taken by the scanner 22, the user will pause the scanner 22 in order to permit a time-wise series of scans to be conducted at that point. These scans are relayed sequentially to the image processing submodule 24 which, in turn, relays a series of processed images to the image selection submodule 26. The image selection submodule 26 will review this series of images until an image that was scanned at an optimal time is found. This optimally-timed image is then relayed to the memory 28 by image selection submodule 26. The image selection submodule 26 also signals to the operator that an optimally-timed image has been obtained, and the operator can then move the scanner 22 to the next cross-section to be scanned along the path to be taken by the scanner 22.

It is possible that the orientation of the scan will change from cross-section to cross-section along the path. Accordingly, the positioning of each scan is recorded using six coordinates—three to represent the spatial coordinates of the cross-section and three to represent its orientation. This information is included with the associated optimally-timed image for the cross-section.

The computer system also includes a monitor 30 that can display various images processed by the image processing submodule 24 based on the scanned data obtained from the scanner 22, as well as images that are saved in memory 28.

Figure 2:
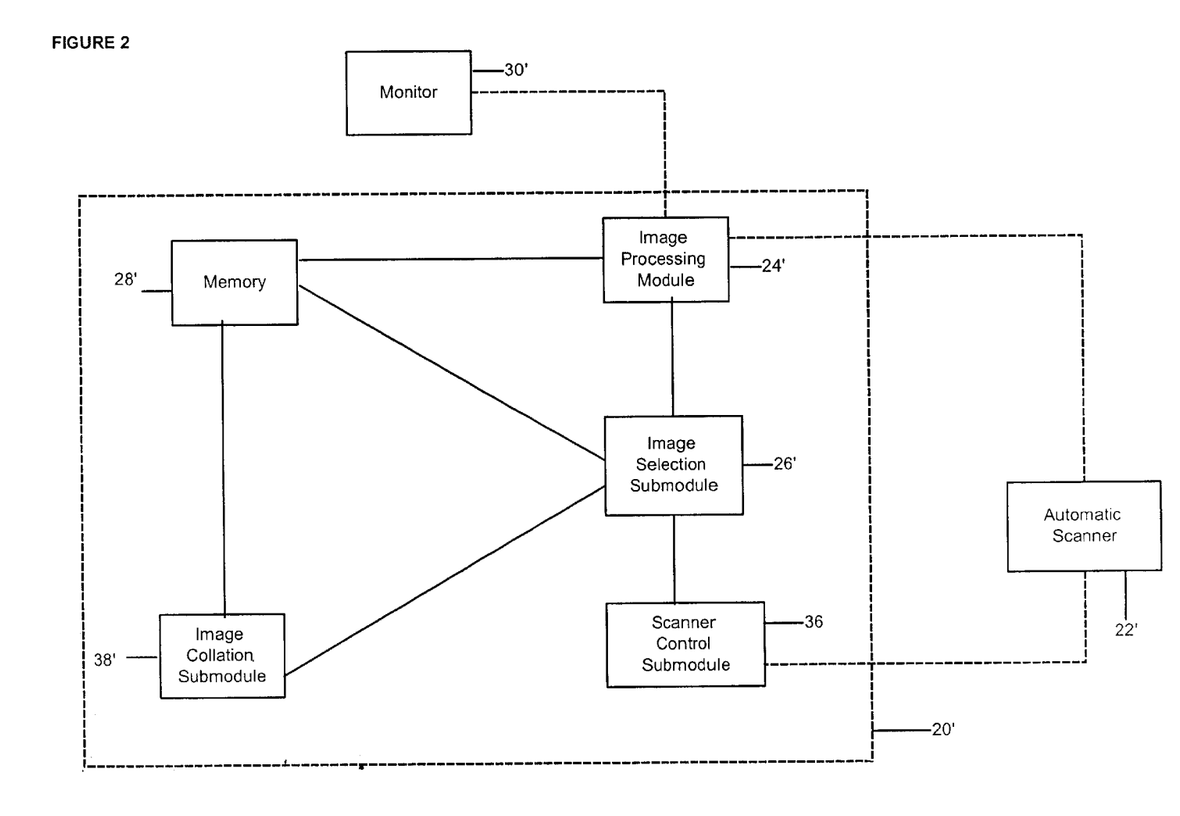
FIG. 2 is a block diagram showing a second system for obtaining an optimal image of a part of a patient according to a second embodiment of the present invention.

Optionally, the computer system may be automated. Referring to FIG. 2, there is illustrated a computer system 20' for controlling a scanner 22' to obtain images of a patient at an optimal time in accordance with a second preferred embodiment of the invention. The computer system of FIG. 2 comprises an automatic scanner 22' that is linked to an image processing submodule 24' of the system 20'. The automatic scanner 22' is operable to scan different cross-sections along a defined path. The image processing submodule 24' is, in turn, linked to an image selection submodule 26', which is linked to a memory 28'. The memory 28' is linked to an image collation submodule 38'. The computer system 20' additionally includes a scanner control submodule 36 linked to the image selection submodule 26'.

In the embodiment of FIG. 2, the scanner 22' automatically moves along the path to the next cross-section to be scanned. Specifically, when the image selection submodule 26' determines that an optimal image has been scanned, a signal is sent to the scanner control submodule 36 instructing the automatic scanner 22' to move to the next cross-section to be scanned or to end the scan when the end of the path has been reached.

Figure 3:
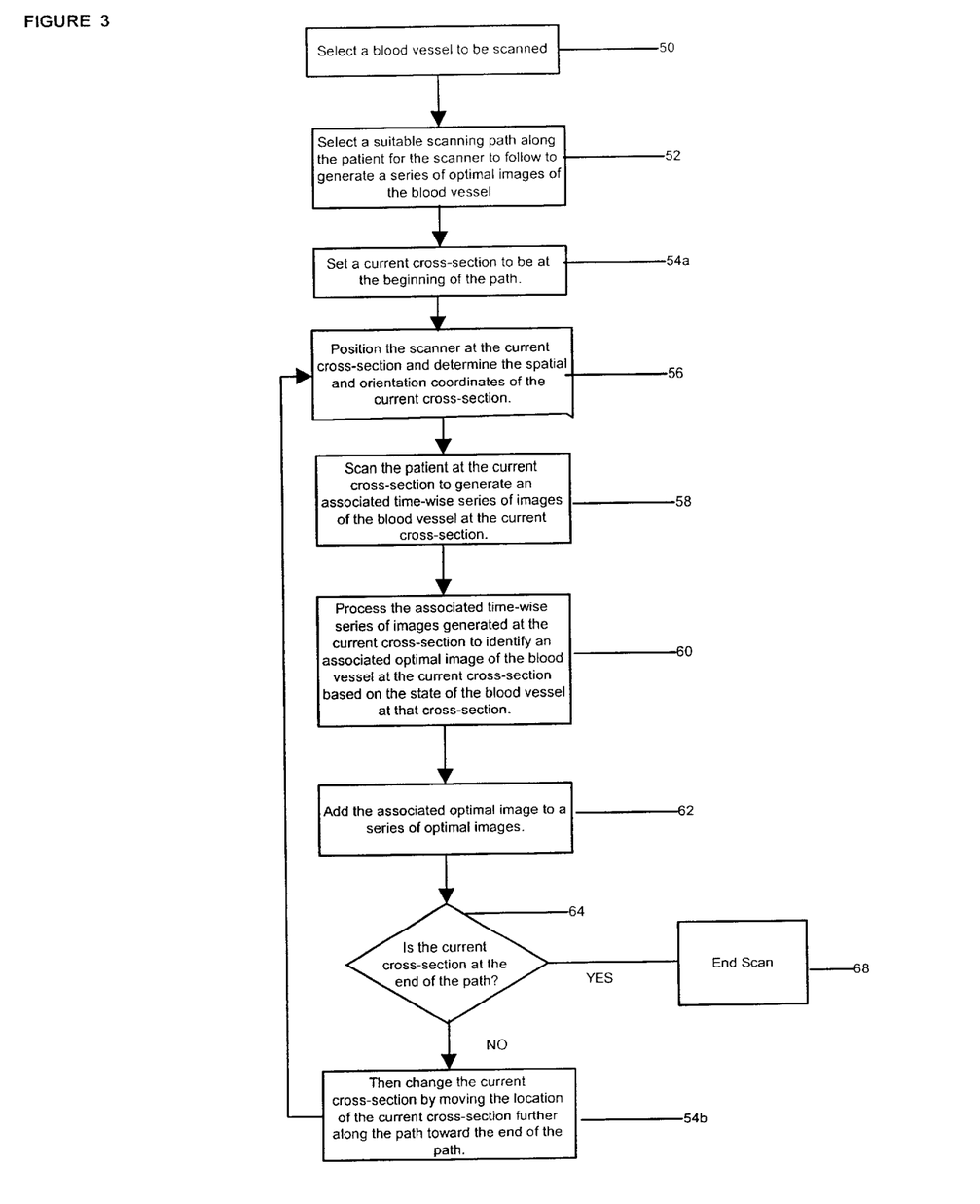
FIG. 3 is a flowchart of steps to be executed in a method of obtaining an optimal image of a selected part of a patient in accordance with an aspect of the present invention.

In FIG. 3, a flowchart shows the steps of a method of obtaining a lengthwise series of cross-sectional images of a blood vessel, in which the blood vessel is shown dilated in all of the cross-sectional images.

In step 50 of the method of FIG. 3, a blood vessel is selected. Then, in step 52, a path is selected relative to the patient along which the scan will occur. This path has a beginning point and an end point, and will be scanned by moving the scanner along the path. The first scan will be taken at a beginning cross-section at the beginning point. The remaining steps of the flowchart are described relative to a current scanning cross-section that is initially defined to be the beginning cross-section. After the beginning point is scanned, the current cross-section is redefined to be at a new point further along the path towards the end of the path. In an analogous way, the current cross-section will be successively redefined to be at each point in a series of points each of which is further along the path than the former current cross-sections. The scan will end when the path has been scanned at cross-sections along its entire length.

The current scanning cross-section is selected according to steps 54a and 54b, which specify beginning conditions and ending conditions of the method respectively. Specifically, step 54a specifies that the current cross-section initially be set to be at the beginning of the scanning path as defined in step 52, while step 64 queries whether the current cross-section, after the scan has taken place, is at the end of the path. If the current cross-section is not at the end of the path, then the current cross-section is changed to be a new cross-section closer to the end of the path in step 54b. If in query 64, the current cross-section is at the end of the path, then the scan is ended as shown in step 66.

Once the path has been defined, and the current cross-section has been selected, the scanner is positioned to scan the blood vessel at the current cross-section, and the spatial and orientation coordinates of the current cross-section are recorded as indicated in step 56 of the flowchart of FIG. 3. As shown in step 58, the blood vessel is scanned at the current cross-section to generate an associated time-wise series of images of the current cross-section. In step 60, the associated time-wise series of images are processed to identify at least one cross-section specific optimal image of the blood vessel at the current cross-section based on the state of the blood vessel at the current cross-section.

As specified in step 62 of the flowchart of FIG. 3, this associated optimal image is then added to the series of optimal images already recorded, or, if the associated optimal image is for the beginning cross-section, then the associated optimal image is the first image to be added to the series of optimal images. Then, as previously discussed in connection with setting the current cross-section, the current cross-section is checked to see if it is at the end of the scan path as specified by query 64 of the flowchart of FIG. 3. If the current cross-section is at the end of the scan path, then the scan is ended, as shown in step 66, while if the current cross-section is not at the end of the scan path, then the current cross-section is changed to be a new cross-section that is further along the path towards the end of the path, as shown in step 54b.

It is possible that the orientation of the scan will change from cross-section to cross-section along the path. Accordingly, in step 56 the positioning of each scan is recorded using six coordinates—three to represent the spatial coordinates of the cross-section and three to represent its orientation. This information is included with the associated time-wise series of images generated in step 60.

Figure 4:
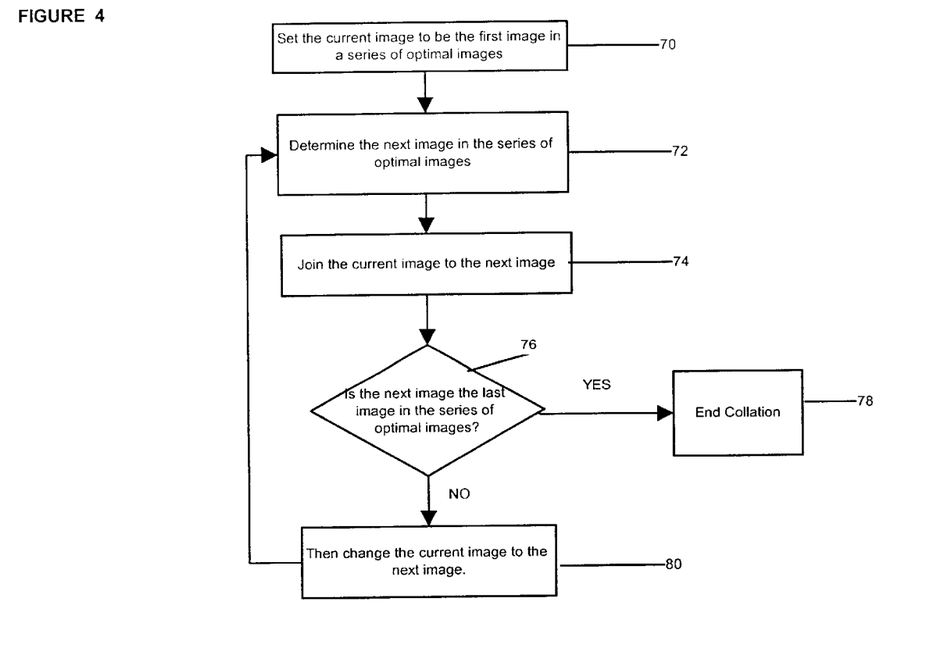
FIG. 4 is a flowchart of steps to be executed in a method of collating a lengthwise series of optimal images selected according to the flowchart of FIG. 3 in accordance with a further aspect of the present invention.

Referring to FIG. 4, there is illustrated a flowchart of a method of collating the optimal images obtained in the method of FIG. 3 in accordance with a preferred aspect of the present invention. Specifically, in step 70 of the flowchart of FIG. 4, a current image is set to be the first image in a series of optimal images. Then, in step 72, the next image in the series of optimal images is determined—the next image will be the image obtained of the next cross-section along the path of the selected part of the patient. In step 74 the current image and the next image, which are both two dimensional images, are joined to define a volume, thereby forming a single three-dimensional image. Query 76 returns the answer "NO" if the next image is not the last image in the series of optimal images, in which case the method proceeds to step 80. In step 80, the current image is changed to be the next image, following which the method returns to step 72. If, on the other hand, query 76 returns the answer "YES" as the next image is the last image in the series of optimal images then the collation is ended in step 78.

Following this process, each of the images is connected to its adjacent image, resulting in a single three-dimensional image of the selected part.

Figure 5:
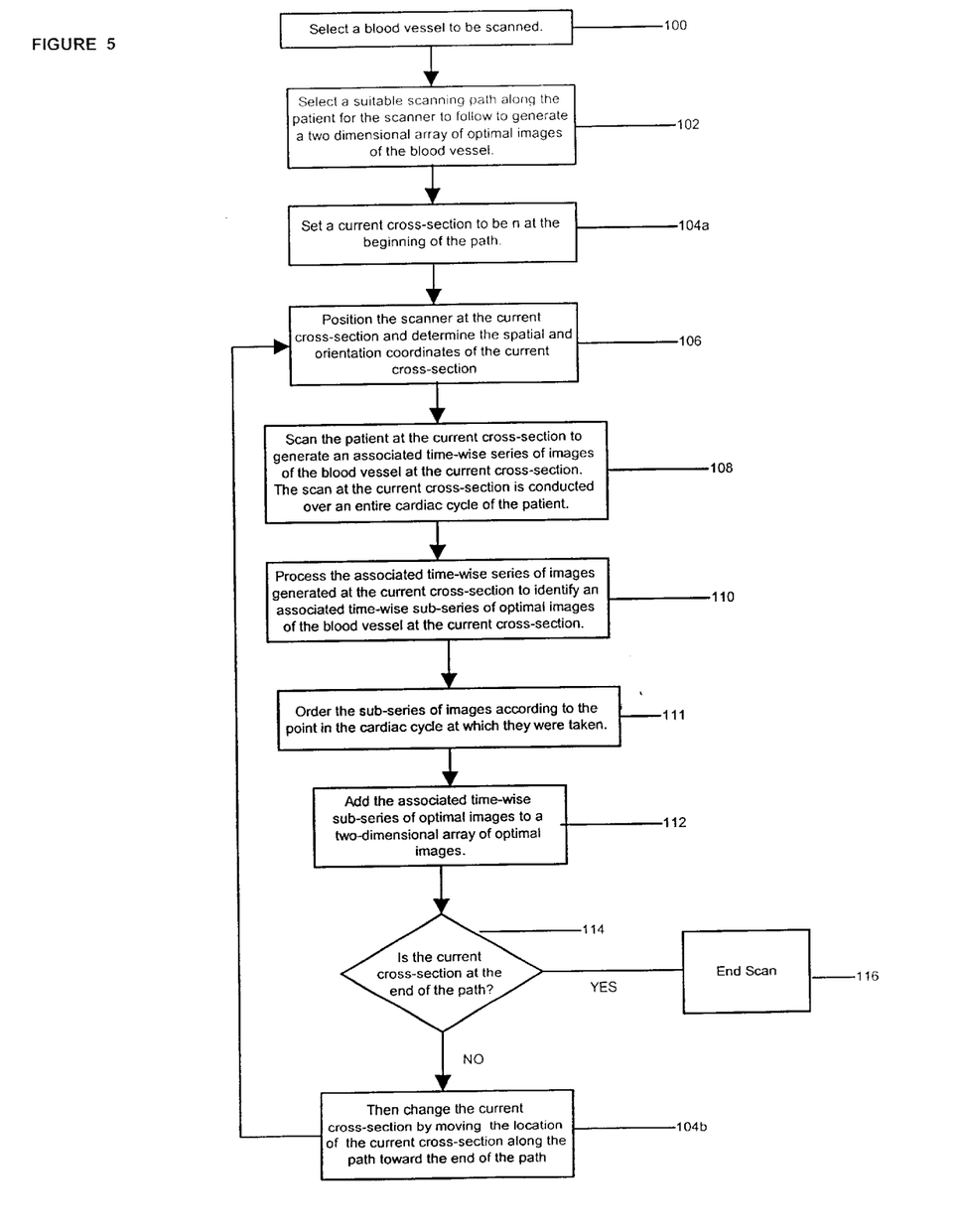
FIG. 5 is a flowchart of steps to be executed in a method of obtaining an optimal time-wise series of images for each cross-section in a series of cross-sections of a selected part of the patient in accordance with an aspect of the present invention.

Referring to FIG. 5, there is illustrated a method of obtaining, at each point in a series of points along the scanning path, an associated time-wise sub-series of optimal images of cross-sections of the selected part in accordance with an embodiment of the invention. In step 100, a blood vessel to be scanned is selected. Then, in step 102, a suitable scanning path along the patient for the scanner to follow to generate optimal images of the blood vessel is determined. As with the path of FIG. 3, the path of FIG. 5 will have a beginning point and an end point and will be scanned by moving the scanner along the path. The first scan will be taken at a beginning cross-section at the beginning point The remaining steps of the flowchart are described relative to a current cross-section that is initially defined to be at the beginning point. After the beginning point is scanned, the current-cross-section is redefined to be at a point closer to the end of the path. The current cross-section is successively redefined to be at a series of points each of which is closer to the end of the path than the immediately preceding point at which the last scan was done. The scan will end when the current cross-section is at the end of the path.

The current cross-selection is selected according to steps 104a and 104b which specify beginning conditions and ending conditions of the method respectively. Specifically, step 104a specifies that the current cross-section initially be set to be at the beginning of the scanning path as defined in step 102, while step 114 queries whether the current cross-section, after the scan has taken place, is at the end of the path. If the current cross-section is not at the end of the path, then the current cross-section is changed to be further along the path towards the end cross-section as shown in step 104b, while if the unchanged current cross-section is at the end of the path, then the scan is ended as shown in step 116.

Once the path has been defined, and the current cross-section has been selected, the scanner is positioned to scan the blood vessel at the current cross-section in step 106 of the flowchart of FIG. 5. In step 108, the blood vessel is scanned at the current point to generate a time-wise series of images of the current cross-section. This scan of the current cross-section is conducted over an entire cardiac cycle of the patient. In step 110, the time-wise series of images at the current cross-section are processed to identify an associated time-wise sub-series of optimal images of the blood vessel at the current cross-section. In step 111, the sub-series of optimal images are then ordered in a definite order depending on the point in the cardiac cycle at which they were taken. For example, the image of the blood vessel minimally dilated can be placed first in the sub-series followed by images of the blood vessel as it gradually dilates, each of which images is more dilated than the image preceding it in the sub-series, until the maximally dilated image is reached. The maximally dilated image in the sub-series is followed by images of the blood vessel as it gradually contracts, each of which images is more contracted than the image preceding it in the sub-series, until the minimally dilated image is once again reached. It will, of course, be appreciated by those skilled in the art that any order will do, provided that the order is the same for the sub-series of images for different cross-sections.

As specified in step 112 of the flowchart of FIG. 5, this associated time-wise sub-series of optimal images is then added to a matrix of optimal images. The matrix is a two-dimensional array, each row of which corresponds to a particular cross-section, and each column of which corresponds to a particular point in the cardiac cycle and to a particular place in the order of each of the time-wise sub-series of optimal images. Then, as previously discussed in connection with setting the current cross-section, the current cross-section is checked to see if the current cross-section is at the end of the path in step 114 of the flowchart of FIG. 5. If the current cross-section is at the end of the path, then the scan is ended in step 116. If the current cross-section is not at the end of the path, then the current cross-section is changed to be further along the path in step 104b, and, in step 106, the scanner is positioned at this new current cross-section.

Figure 6:
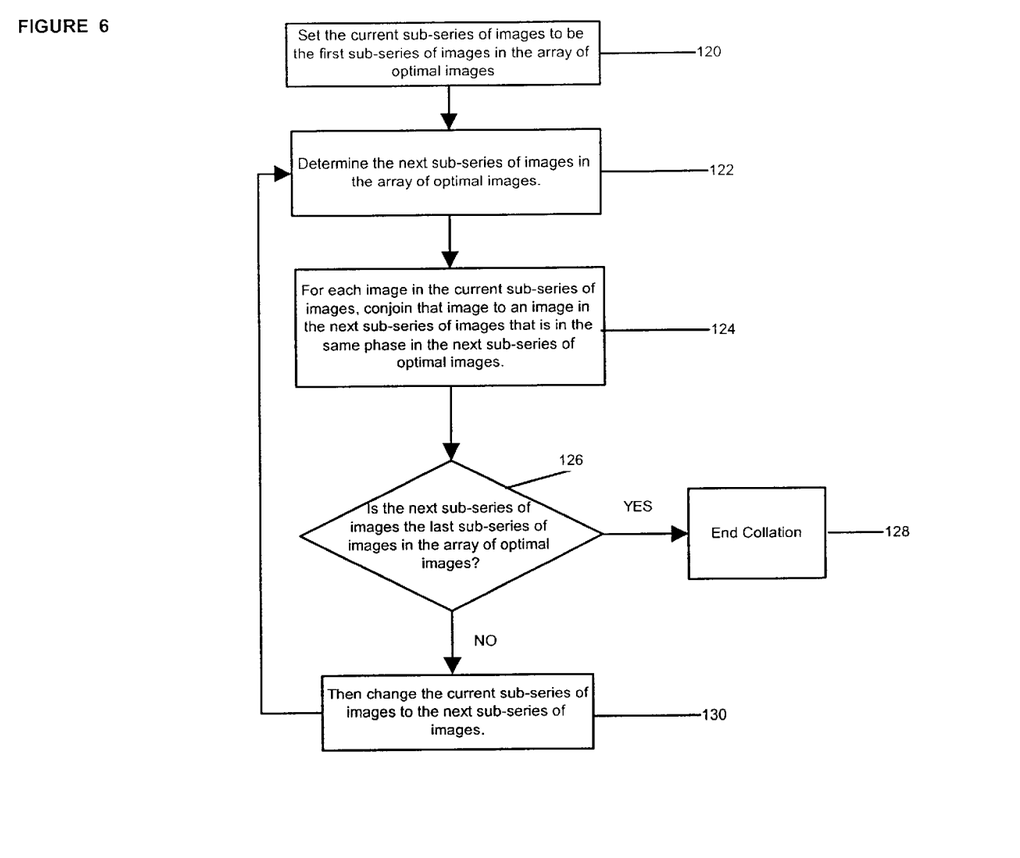
FIG. 6 is a flowchart of steps to be executed following execution of the method of FIG. 5 to conjoin the optimal time-wise series of images obtained from adjacent cross-sections of the selected part of the patient in accordance with a further aspect of the present invention.

Referring to FIG. 6, there is illustrated a flowchart of steps to be executed, after the method of FIG. 5 has been executed, to collate all of the optimal images in the same column of the two dimensional array of steps 112 of FIG. 5 in accordance with an aspect of the invention. Specifically, in step 120, the collation method is initialized by setting a current sub-series of images to be the first sub-series of images in the array of optimal images. Then, in step 122, the next sub-series of images in the array of optimal images is determined. In step 124 each image occupying a place in the current sub-series of images is conjoined to an image in the next sub-series of images that occupies the same place in the next sub-series of images. This can also be expressed relative to the two dimensional array. Specifically, as described above, the two dimensional array stores all of the images in the associated time-wise sub-series of optimal images of the blood vessel for one cross-section in a single row. Further, optimal images taken of different cross-sections during the same period in the cardiac cycle are stored in the same column. The associated time-wise sub-series of optimal images of the blood vessel at adjacent cross-sections are stored in adjacent rows. Accordingly, in step 124, each image in a current row of the two dimensional array is conjoined to the image stored in the same column of the next row of the two dimensional array.

Following step 124, query 126 returns the answer "YES" if the next sub-series of images is the last sub-series of images in the array of optimal images. The collation method of FIG. 6 then proceeds to step 128 in which the collation is ended. If the next sub-series of images is not the last sub-series of images in the array of optimal images, then query 126 returns the answer "NO" and the method proceeds to step 130 of the flowchart of FIG. 6. In step 130, the current sub-series of images is changed to be the next sub-series of images, after which the method returns to step 122.

The present invention may be implemented in other specific forms without departing from the spirit or the essential characteristic thereof. Certain adaptations and modifications of the invention will be obvious to those skilled in the art. For example, while the foregoing description has described the invention in relation to scanning a blood vessel, it will be appreciated by those skilled in the art that the invention is also applicable to scanning other parts of the body. Therefore, the presently discussed aspects are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A method of obtaining an optimal image of a selected part of a patient being scanned, wherein the selected part varies cyclically over time, comprising the steps of:

scanning the selected part to obtain a time-wise series of images of the selected part;

analyzing each image in the time-wise series of images to determine a state of the selected part as shown in that image of the time-wise series of images; and selecting a selected image from the time-wise series of images based on the state of the selected part in the selected image.

2. The method as defined in claim 1 wherein
the selected part is a blood vessel;

the time-wise series of images is analyzed to determine dilation of the blood vessel; and, the selected image is selected from the time-wise series of images to show the blood vessel based on dilation of the blood vessel.

3. The method as defined in claim 2 wherein the selected image is selected from the time-wise series of images to show the blood vessel when the blood vessel is maximally dilated.

4. The method as defined in claim 2 wherein the step of selecting the selected image from the time-wise series of images comprises measuring a cross-sectional area of the selected part in each image in the time-wise series of images; and selecting the selected image to have a maximum cross-sectional area.

5. A method of obtaining a plurality of images of a selected part of a patient being scanned by scanning the patient at a plurality of cross-sections, wherein the selected part varies cyclically over time, comprising the steps of, at each cross-section in the plurality of cross-sections, (a) scanning the patient to obtain an associated time-wise series of images of the selected part, (b) for each image in the associated time-wise series of images, analyzing the image to identify an state of the selected part at the cross-section, and (c) selecting an associated selected image from the associated time-wise series of images based on the state of the selected part at the cross-section in the associated selected image.

6. The method as defined in claim 5 further comprising collating the associated selected image of the selected part for each cross-section in the plurality of cross-sections to obtain an aggregate image composed of the plurality of selected images for the plurality of cross-sections.

7. The method as defined in claim 6 wherein the selected part varies cyclically based on a selected cycle of the patient;

for each cross-section in the plurality of cross-sections, the step of scanning the patient to obtain the associated time-wise series of images extends over the selected cycle of the patient, and the step of selecting an associated optimal image comprises selecting an associated time-wise sub-series of optimal images for representing the cross-section over the selected cycle; and, the step of collating the associated optimal image of the selected part for each cross-section comprises conjoining each image in the associated time-wise sub-series of optimal images to an image in the associated time-wise sub-series of optimal images for an adjacent cross-section, the conjoined images having been captured at substantially the same point within the selected cycle.

8. The method as defined in claim 7 wherein the selected cycle of the patient is a cardiac cycle of the patient.

9. The method as defined in claim 8 wherein the selected part of the patient is one of a blood vessel and a heart of the patient.

10. The method as defined in claim 5 further comprising defining a scanning path on the patient before commencing the scan;

selecting the plurality of cross-sections to be a series of cross-sections on the scanning path; and for each cross-section in the series of cross-sections before a final cross-section on the path, moving to the next cross-section in the series of cross-sections along the path after the associated optimal image is identified.

11. The method as defined in claim 10 wherein the selected part is a blood vessel;

the associated time-wise series of images for each cross-section is analyzed to determine dilation of the blood vessel; and, for each cross-section, the associated selected image is selected from the associated time-wise series of images based on dilation of the blood vessel.

12. The method as defined in claim 11 wherein the associated selected image is selected from the associated time-wise series of images to show the blood vessel maximally dilated.

13. A scanning system for obtaining an optimal image of a selected part of a patient, wherein the selected part varies cyclically over time, comprising scanning means for scanning a cross-section of a selected part of the patient to generate a time-wise series of images of the cross-section;

image processing means for analyzing the time-wise series of images to determine a state of the selected part as shown in each image in the time-wise series of images;

image selection means for selecting the optimal image from the time-wise series of images based on the state of the selected part in the optimal image; and, memory for storing the optimal image.

14. The system as defined in claim 13 wherein the selected part is a blood vessel;

the image processing means is operable to analyze the time-wise series of images to determine dilation of the blood vessel; and, the image selection means is operable to select the selected image from the time-wise series of images based on the dilation of the blood vessel.

15. The system as defined in claim 14 wherein the image selection means is operable to select the selected image from the time-wise series of images to show the blood vessel when the blood vessel is maximally dilated.

16. The system as defined in claim 14 wherein the image processing means is operable to measure a cross-sectional area of the selected part in each image in the time-wise series of images; and, the image selection means is operable to select the selected image to have a maximum cross-sectional area.

17. The system as defined in claim 13 wherein the scanner is operable to scan the selected part at a plurality of cross-sections to generate a time-wise series of images of each cross-section in the plurality of cross-sections;

the image processing means is operable to analyze the time-wise series of images of each cross-section in the plurality of cross-sections to determine an associated state of the selected part as shown in each image in the time-wise series of images;

the image selection means is operable to select an associated optimal image from the time-wise series of images of each cross-section in the plurality of cross-sections based on the state of the selected part in the optimal image; and, the memory is operable to store a plurality of optimal images comprising the associated optimal image of each cross-section in the plurality of cross-sections.

18. The system as defined in claim 17 further comprising collation means for collating the associated selected image of the selected part for each cross-section in the plurality of cross-sections to obtain an aggregate image composed of the plurality of selected images for the plurality of cross-sections.

19. The system as defined in claim 18 further comprising scanner control means for, defining a scanning path on the patient before commencing the scan, the plurality of cross-sections being on the scanning path; and, for each cross-section in the series of cross-sections before a final cross-section on the path, moving to the next cross-section in the series of cross-sections along the path after the associated optimal image is identified.

20. The system as defined in claim 17 wherein the selected part varies cyclically based on a selected cycle of the patient;

the scanning means is operable to scan each cross-section in the plurality of cross-sections over the selected cycle of the patient to obtain the associated time-wise series of images, and the image selection means is operable to select an associated time-wise sub-series of optimal images to represent the cross-section over the selected cycle; and, the collation means is operable to conjoin each image in the associated time-wise sub-series of optimal images to an image in the associated time-wise sub-series of optimal images for an adjacent cross-section, the conjoined images having been captured at substantially the same point within the selected cycle.

* * * * *